US008052720B2

(12) United States Patent
Kuester et al.

(10) Patent No.: US 8,052,720 B2
(45) Date of Patent: Nov. 8, 2011

(54) MINIMALLY INVASIVE PEDICLE SCREW ACCESS SYSTEM AND ASSOCIATED METHOD

(75) Inventors: W. Matthew Kuester, St. Louis Park, MN (US); Hugh D. Hestad, Edina, MN (US); Joseph Aferzon, New Britain, CT (US); Paul Hickey, Eden Prairie, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 1201 days.

(21) Appl. No.: 11/558,060

(22) Filed: Nov. 9, 2006

(65) Prior Publication Data

US 2008/0114403 A1   May 15, 2008

(51) Int. Cl.
*A61B 17/70* (2006.01)
(52) U.S. Cl. .................................................. 606/246
(58) Field of Classification Search ............. 606/245, 606/264, 265, 266, 267, 271, 278, 279, 300, 606/301, 86 R, 104, 86 A; 600/201, 203
See application file for complete search history.

(56) References Cited

U.S. PATENT DOCUMENTS

| | | | |
|---|---|---|---|
| 5,242,443 A * | 9/1993 | Kambin | 606/60 |
| 6,235,028 B1 | 5/2001 | Brumfield et al. | |
| 6,951,538 B2 | 10/2005 | Ritland | |
| 7,008,424 B2 | 3/2006 | Teitelbaum | |
| 7,250,052 B2 | 7/2007 | Landry et al. | |
| 2004/0039384 A1 | 2/2004 | Boehm, Jr. et al. | |
| 2004/0138662 A1 | 7/2004 | Landry et al. | |
| 2004/0143265 A1 | 7/2004 | Landry et al. | |
| 2004/0172022 A1 | 9/2004 | Landry et al. | |
| 2005/0065517 A1 * | 3/2005 | Chin | 606/61 |
| 2005/0131408 A1 | 6/2005 | Sicvol et al. | |
| 2005/0131421 A1 | 6/2005 | Anderson et al. | |
| 2005/0182407 A1 | 8/2005 | Dalton | |
| 2005/0182410 A1 * | 8/2005 | Jackson | 606/73 |
| 2005/0192589 A1 | 9/2005 | Raymond et al. | |
| 2005/0215999 A1 | 9/2005 | Birkmeyer et al. | |
| 2005/0228380 A1 | 10/2005 | Moore et al. | |
| 2005/0234449 A1 | 10/2005 | Aferzon | |
| 2006/0036252 A1 | 2/2006 | Baynham et al. | |
| 2006/0247630 A1 | 11/2006 | Iott et al. | |

(Continued)

OTHER PUBLICATIONS

Zimmer Spine, Silhouette Spinal Fixation System, Catalog, Mar. 2005, 6 pgs.

*Primary Examiner* — Eduardo C Robert
*Assistant Examiner* — Summer Kostelink
(74) *Attorney, Agent, or Firm* — Seager Tufte Wickhem LLC

(57) ABSTRACT

A spinal fixation access system includes a pedicle screw with extended tabs that form a single solid pedicle screw assembly. The surgical procedure associated with this invention involves making small, discrete incisions for the placement of select pedicle screws. The extended tabs of the pedicle screws retract soft tissue, muscle and the like to thereby provide visibility and access to the head of the pedicle screw. Through the extended tabs, instrumentation such as a spine rod, set screw and other required hardware may be delivered to the pedicle screws. A collar may be coupled around the extended tabs to provide stability to the construct and a platform for additional components of this invention. Once a spine rod is secured to the pedicle screws, a frangible joint joining the tabs to the pedicle screw assembly is broken off using appropriate instrumentation and the extended tabs may be removed.

16 Claims, 4 Drawing Sheets

U.S. PATENT DOCUMENTS

| | | |
|---|---|---|
| 2007/0106123 A1 | 5/2007 | Gorek et al. |
| 2007/0233079 A1* | 10/2007 | Fallin et al. .................. 606/61 |
| 2007/0288026 A1* | 12/2007 | Shluzas ........................ 606/73 |
| 2007/0299443 A1 | 12/2007 | DiPoto et al. |
| 2008/0082103 A1 | 4/2008 | Hutton et al. |
| 2008/0119849 A1 | 5/2008 | Beardsley et al. |
| 2008/0125817 A1* | 5/2008 | Arnett et al. ................ 606/319 |
| 2008/0262318 A1 | 10/2008 | Gorek et al. |
| 2008/0300638 A1 | 12/2008 | Beardsley et al. |

* cited by examiner

MINIMALLY INVASIVE PEDICLE SCREW ACCESS SYSTEM AND ASSOCIATED METHOD

BACKGROUND

This invention relates generally to spinal fixation devices and more specifically relates to a system and associated method for minimally invasive installation of pedicle screws and spinal rods of spinal fixation constructs.

The human spinal column is a highly complex system of bones and connected tissues that provide support for the body and protects the delicate spinal cord and nerves. The spinal column includes a series of vertebrae stacked one atop the other. Each vertebral body includes a relatively strong cortical bone portion forming the outside surface of the body and a relatively weak cancellous bone portion forming the center of the body. An inter-vertebral disc is situated between each vertebral body that provides for cushioning and dampening of compressive forces applied to the spinal column. The vertebral canal containing delicate spinal cords and nerves is located just posterior to the vertebral bodies.

A variety of types of spinal column disorders may be caused by abnormalities, disease, trauma or the like and result in debilitating pain as well as diminished nerve function in many cases. One known technique to address many such spinal conditions is commonly referred to as spinal fixation. Surgical implants are used for fusing together and/or mechanically immobilizing adjacent vertebrae of the spine. Spinal fixation may also be used to improve the position of the adjacent vertebrae relative to one another so as to alter the overall alignment of the spine. Such techniques have been used effectively to treat many spinal conditions and to relieve pain suffered by the patient.

One particular spinal fixation technique includes immobilizing the spine by using orthopedic spine rods which run generally parallel to the spine. Exposing the spine posteriorly and fastening hooks or bone screws to the pedicles of the appropriate vertebrae accomplish this. The pedicle anchors or screws are generally placed two per vertebrae, one at each pedicle on either side of the spinal column and serve as anchor points for the spine rods. The aligning influence of the rods forces the spine to conform to a more desirable shape. In many cases, the spine rods are bent to achieve the desired curvature of the spinal column.

Installation of such spinal fixation constructs conventionally requires a surgeon to prepare a long incision aligned with the spinal column of a patient. The pedicle screws, hooks or other anchors are then inserted into a number of vertebrae after which the spine rod is located with respect to saddles or U-shaped channels attached to the pedicle screws. The spine rod is then bent to match the relative position of the pedicle screw heads. Visualization of the accuracy of the alignment of the spine rod and the screw heads may be difficult because of visual interference from tissue and blood in the surgical field. Conventional surgical methods require a large midline incision and retraction of skin, muscle and other tissue to provide the surgeon with sufficient visualization of the pedicle bone structure.

Bending of the spine rod is performed once the screws are placed into the vertebrae and, therefore, visualization of the accuracy of the placement and configuration of the spine rod is very difficult. Improper alignment and inaccurate bending of the spine rod decreases the effectiveness of the fixation construct and often increases the surgical difficulty and time required for the surgery. In combination with the relatively long incision required for the installation of the spine rod, extended surgical procedures and related difficulties or complications are generally recognized as major contributing influences for extended patient recovery and less than optimal spinal fixation results.

SUMMARY OF THE INVENTION

This invention addresses these and other shortcomings in the prior art. The devices and methods associated with this invention are used to aid in the surgery for vertebral stabilization using pedicle hooks, screws, anchors and fixation rods.

According to various embodiments of this invention, pedicle screws are inserted into the target vertebrae of a patient's spinal column. The pedicle screw may be cannulated for proper positioning and installation. In one aspect, this invention provides an access system which involves a pedicle screw with incorporated extended tabs that form a single solid pedicle screw assembly The surgical procedure associated with this invention involves making small, discrete incisions for the placement of select pedicle screws. The extended tabs of the pedicle screws retract soft tissue, muscle and the like to thereby provide visibility and access to the head of the pedicle screw. Through the extended tabs, instrumentation such as a spine rod, set screw and other required hardware may be delivered to the pedicle screws.

In another aspect of this invention, a collar may be coupled around the extended tabs to provide stability to the construct and a platform for additional components of this invention.

Once the rod is secured with the set screws, a frangible joint joining the tabs to the pedicle screw assembly is broken off using appropriate instrumentation and the extended tabs may be removed. The extended length of the tabs for each pedicle screw extend beyond the surface of the skin (i.e., percutaneously) thereby retracting soft tissue and muscle enabling the surgeon to install the spinal fixation construct with smaller discrete incisions as opposed to an extended incision. As such, a more minimally invasive surgical procedure can be accomplished with this invention thereby allowing for visualization of the installation components during the surgery and promoting patient recovery post-surgery. Additionally, the extended tabs provide an indication to the surgeon of the configuration of the patient's vertebrae thereby enabling the surgeon to pre-bend the spine rod prior to insertion into the patient. The spine rod is inserted into the patient in a minimally invasive procedure through slots provided in the tabs and associated collars when coupled with the tabs.

This invention is to be distinguished from reduction screws that are often used in correcting spinal problems, particularly reducing various grades of spondylolisthesis (anteriorly dislocated vertebrae). Reduction screws do not typically reach beyond the skin's surface when installed, whereas this invention is intended to provide minimally invasive access and soft tissue retraction during installation of a spinal construct. The tabs of this invention are intended to extend beyond the skins surface, independently or in conjunction with the telescoping collar. The extended threads on a reduction screw allows for a set screw engagement with the pedicle screw head to provide leverage against the rod to reduce the vertebral dislocation. On the other hand, the extended tab and pedicle screw combination of this invention allows for set screw engagement to fully seat the rod by pushing it into position.

As a result of these and other aspects of this invention, increased efficiency and accuracy is provided for installation of a spinal fixation construct in a minimally invasive atmosphere thereby promoting patient recovery and optimum spinal surgery results.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein.

DETAILED DESCRIPTION OF THE INVENTION

Figure 1:
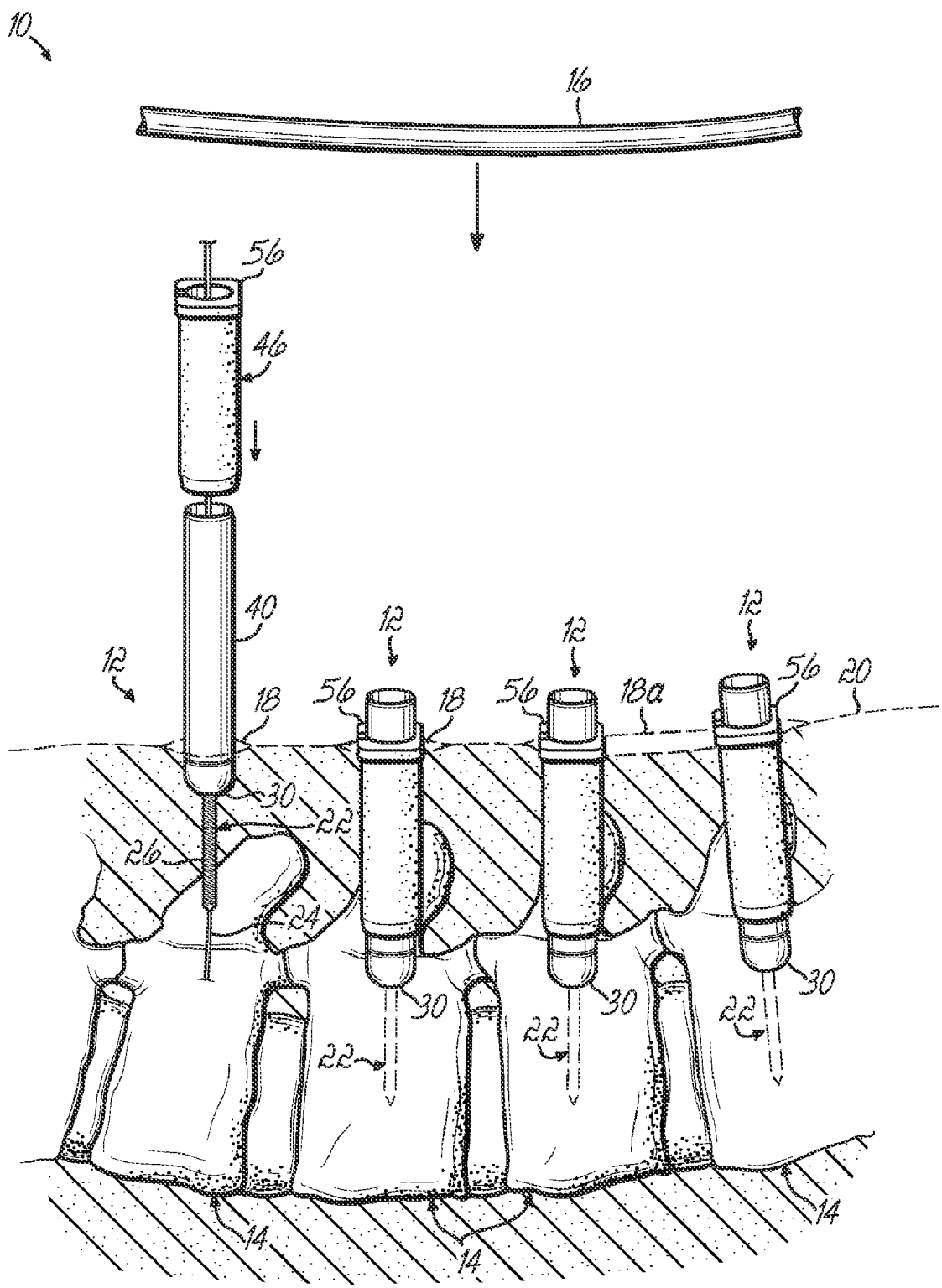
FIG. 1 is a side elevational and partial cross-sectional view of a spinal fixation construct being surgically implanted in selected vertebrae of a patient's spine according to one embodiment of this invention.
Figure 2:
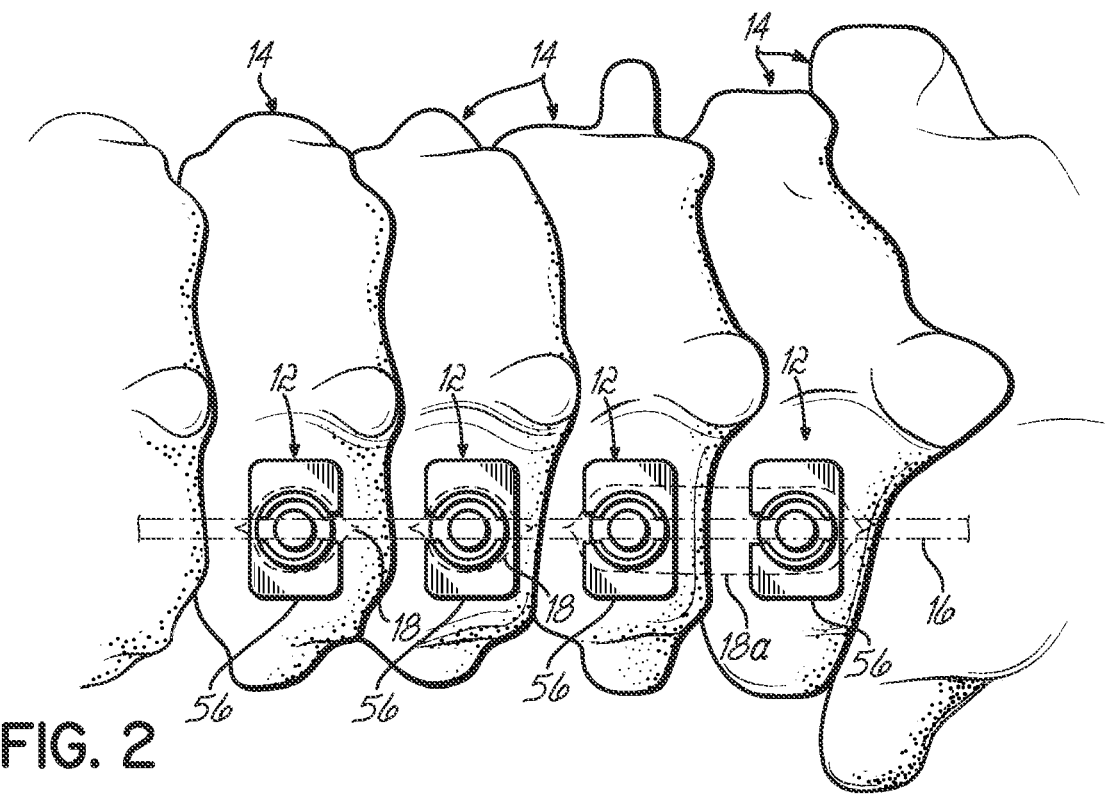
FIG. 2 is top elevational view of the components of a spinal fixation construct as shown in FIG. 1.

Referring to FIG. 1, various embodiments of a minimally invasive spinal fixation construct 10 and associated installation method are shown. The spinal fixation construct 10 includes a number of pedicle screw assemblies 12, each of which is inserted into selected vertebrae 14 of a patient. The pedicle screw assemblies 12 are joined together in the spinal fixation construct by a spine rod 16. According to various aspects of this invention, the individual pedicle screw assemblies 12 may be inserted into the patient through discrete and often individual incisions 18 in the patient's skin 20. In certain instances, a single incision 18a may be available to provide installation of multiple pedicle screw assemblies 12 in adjacent vertebrae 14 as shown in FIGS. 1 and 2. The small, discrete incisions 18 provide the opportunity for insertion of a cannulated pedicle screw 22 via a K-wire 24 inserted through the incision 18 to the precise location on the vertebrae 14 for proper installation of the pedicle screw 22. While cannulated and other pedicle screw assemblies are shown and described herein, one of ordinary skill in the art will appreciate that other types of vertebrae engaging mechanisms can be utilized such as hooks for anchoring the spine rod to the patient's spinal column.

As shown generally in FIGS. 1 and 3A-3D, a pedicle screw assembly 12 according to one embodiment of this invention includes a pedicle screw 22 having a threaded shaft 26 and a distal tip 28 for insertion and stable positioning into the pedicle area of the patient's vertebrae 14. The pedicle screw assembly 12 shown herein is a polyaxial pedicle screw in which a polyaxial body 30 mounted opposite from the distal tip 28 of the screw 22 to a screw head 32 provides for a variety of orientations of the polyaxial body 30 relative to longitudinal axis of the screw 22 as is common with many pedicle screw systems. The polyaxial body 30 coupled to the pedicle screw head 32 includes a saddle or U-shaped channel 34 formed between a pair of spaced arms 36 extending upwardly from the body 30. The polyaxial body 30 is adapted to receive the spine rod 16 in the saddle or U-shaped channel 34 and the spine rod 16 is securely retained by the polyaxial body 30 via a set screw 38 (FIG. 4B) threadably received therein as is common with many known pedicle screw systems.

One aspect of various embodiments of this invention includes tabs 40 extending upwardly from the polyaxial body 30 as shown in FIGS. 1 and 3A-3D. A pair of generally arcuate channel-shaped tabs 40 is each coupled to one of the arms 36 of the polyaxial body 30 via a reduced thickness frangible joint 42. Due to the relative position and configuration of the tabs 40 of the pedicle screw assembly 12 according to one embodiment of this invention, a pair of spaced slots 44 is formed between the tabs 40 and each slot 44 is in communication with the U-shaped channel or saddle 34 of the polyaxial body 30. Advantageously, the tabs 40 are extended to project through the incision 18 such that a distal end of the tabs 40 is located percutaneously above the patient's skin 20 when the pedicle screw 22 is inserted into the vertebrae 14 as shown in FIG. 1.

Another aspect of various embodiments of this invention is also shown in FIGS. 1 and 3A-3D as a collar 46 adapted to slidably couple or telescopically mate with the extended tabs 40 on the pedicle screw assembly 12. The collar 46 in one embodiment includes a generally cylindrical side wall 48 having a circular cross-sectional configuration. The collar 46 includes a tapered distal end 50 as well as a full-length slot 52 adapted to be aligned with one of the slots 44 formed between the tabs 40 of the polyaxial pedicle screw assembly 12. A distal partial slot 54 is positioned diametrically opposite from the full-length slot 52 and is adapted to be aligned with a corresponding slot 44 between the tabs 40 on the pedicle screw assembly 12. The collars 46 are adapted to be telescopically mated with the tabs 40 when the pedicle screw assembly 12 is installed as shown generally in FIGS. 1 and 2.

A proximal flange 56 is formed opposite from the tapered distal end 50 of the collar 46. The flange 56 may have a generally rectangular configuration and adapted to be juxtaposed on top of the patient's skin 20 at the associated incision 18. The collar 46 provides added stability to the construct and a platform for additional devices such as a light attachment (not shown) to increase the visualization of the surgical site. The rectangular or square profile of the flanges 56 on the tops of the telescoping collars 46 assist in avoiding interference between the collars 46 of adjacent levels. In addition, the top surface of the flanges 56 may include a hole, boss or other feature (not shown) that could be used for attachment of an additional instrument for stabilization or alignment of the construct as needed.

Figure 5:
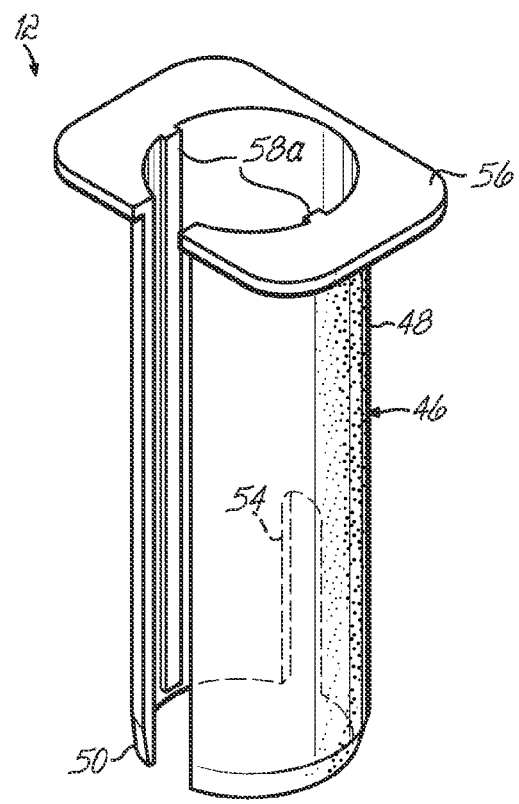
FIG. 5 is an alternative embodiment of a spinal fixation construct according to this invention.
Figure 5:
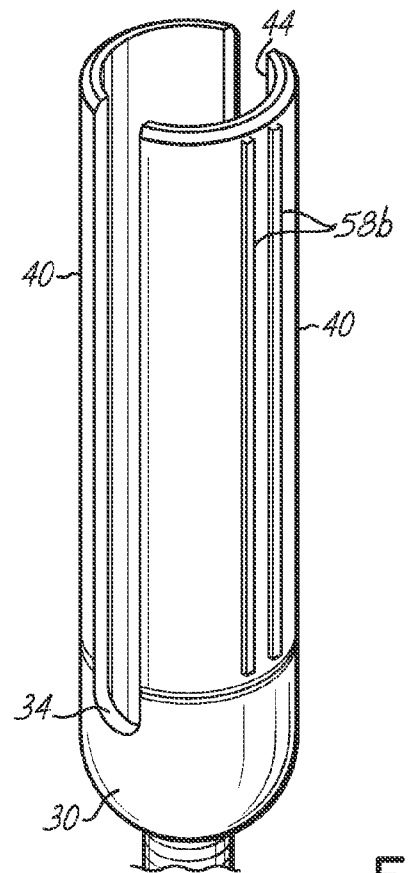

An alternative embodiment of the pedicle screw assembly 12 according to this invention is shown in FIG. 5 in which elements of the invention similar to those of the other embodiments are identified with the same reference numerals. The pedicle screw assembly 12 in FIG. 5 includes a clocking feature that will inhibit rotation of the collar 46 relative to the tabs 40 and thereby hold the orientation of the slots 52, 54 in the collar 46 in line with the slots 44 between the tabs 40. In the embodiment shown in FIG. 5, the clocking feature is provided by two pair of ribs 58b formed on the outer surface of the tabs 40 and a pair of single ribs 58a formed on the inner surface of the collar 46. Each of the single ribs 58a is positioned between one of the pairs of ribs 58b on the collar 46 as the collar 46 slides onto the tabs 40 and the ribs 58b capture the rib 58a there between to inhibit relative rotation between the tabs 40 and the collar 46 to maintain registration of the slots 44, 52, 54. The ribs 58a, 58b are only one embodiment of the clocking feature according to this invention and the clocking feature could be achieved by using cooperating flats on both the screw tabs 40 and telescoping collar 46 to resist relative rotation. Alternatively, the clocking feature may extend only partially along the height of the tabs 40 and/or collar 46 to inhibit relative rotation for some engagement positions of the collar 46 and tabs 40 while permitting relative rotation for other engagement positions.

The telescoping collar 46 not only provides stability to the construct, but also extends the length of retraction in cases where the extended tabs 40 alone do not extend beyond the surface of the skin. The telescoping collar 46 provides for adjustability in the depth of retraction. Additionally, rotation of the collar 46 by about go degrees around the extended tabs 40 allows the telescoping collar 46 to fully seat the rod 16 into the polyaxial body 30.

One advantage provided by this invention is shown generally in FIG. 1. With the pedicle screws 22 inserted into the appropriate vertebrae 14 and the extended tabs 40 and collars 46 projecting from the screw assemblies 12 percutaneously, the relative position of the polyaxial bodies 30 is projected percutaneously. As such, the surgeon may bend the spine rod 16 to conform to the position of the polyaxial bodies 30 installed on the vertebrae 14 according to the relative position of the tabs 40 and collars 46 positioned percutaneously. The enhanced visualization and access afforded by the percutaneous positioning of the tabs 40 and collars 46 in the general orientation of the associated polyaxial bodies 30 is a significant advantage for the accurate and precise positioning and bending of the spine rod 16. Moreover, once the spine rod 16 is appropriately configured, it may be inserted through the slots 44, 52 and 54 and into the saddles 34 of the polyaxial bodies 30. Specifically, one end of the spine rod 16 may be initially inserted into a leading pedicle screw assembly 12 through the slots 44, 52, and 54. This may be accomplished with an incision 18a that is adjacent to a pair of pedicle screw assemblies 12 as shown in FIG. 1. The access slots 44, 52, 54 provided by the tabs 40 and the collars 56 provide communication between the various adjacent pedicle screw assemblies 12 so that the spine rod 16 may be inserted into the saddles 34 of the polyaxial bodies 30 in a minimally invasive and less disruptive procedure than previously realized.

Figure 4A:
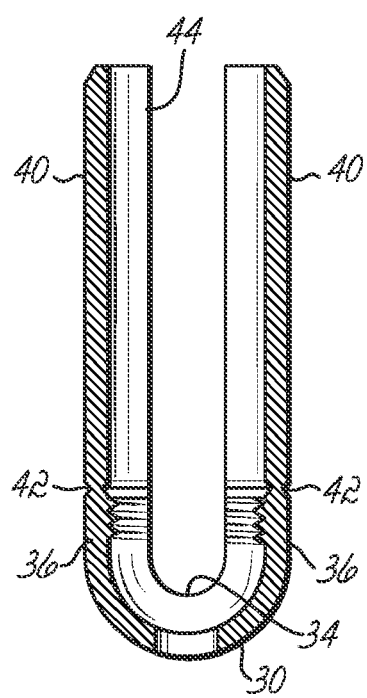
FIG. 4A is a cross-sectional view of a polyaxial head adapted to be used with a pedicle screw according to one embodiment of this invention.
Figure 4B:
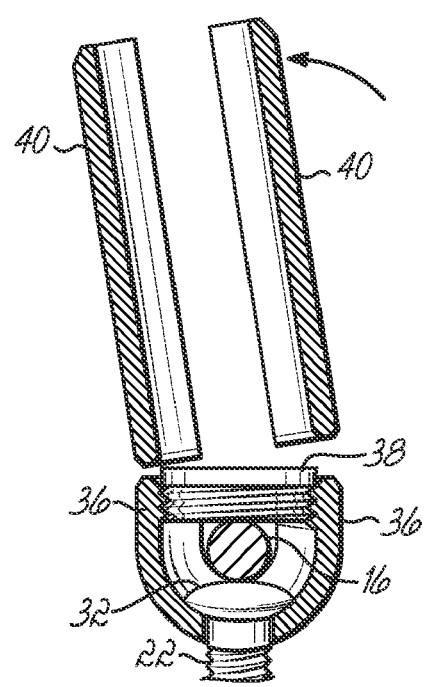
FIG. 4B is a view similar to FIG. 4A with extended tabs on the polyaxial head being removed on a frangible joint according to one embodiment of the invention.
Figure 3A:
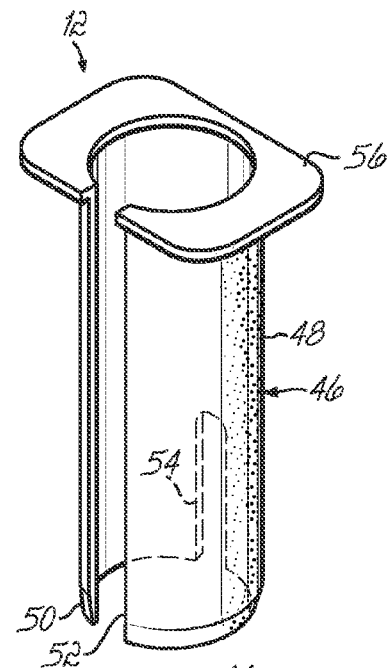
FIGS. 3A-3D are sequential views of a pedicle screw construct being assembled together according to one embodiment of this invention for use in a spinal fixation system.
Figure 3B:
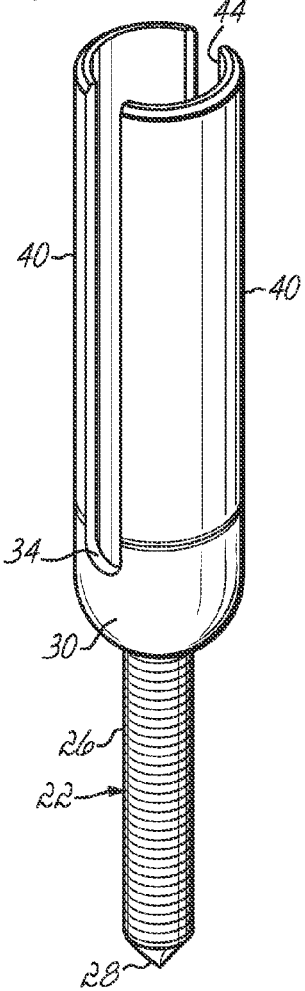
Figure 3C:
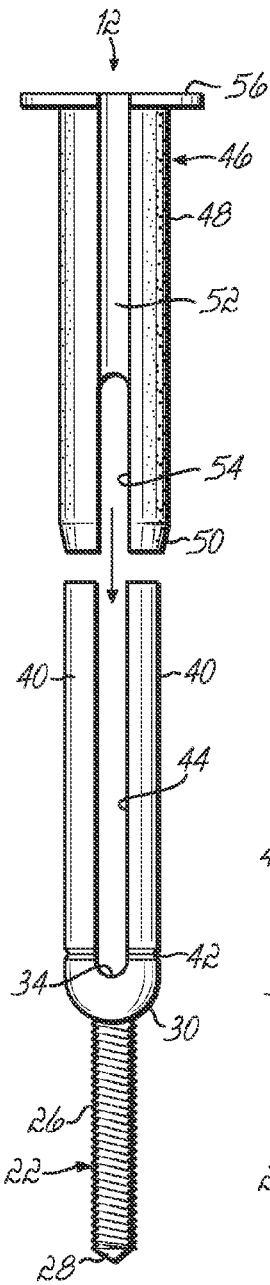
Figure 3D:
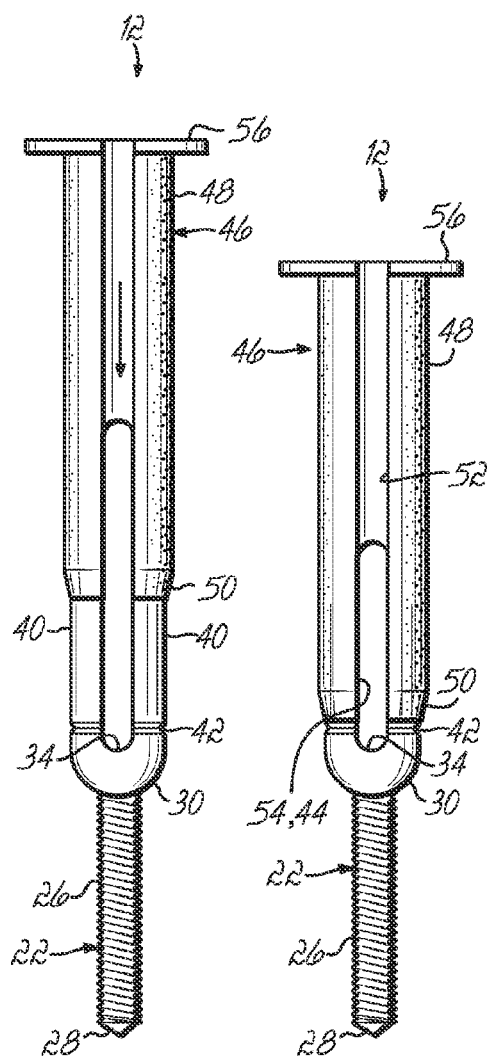

After the spine rod 16 is inserted through the discrete incisions 18 and the slots 44, 52, 54 of the pedicle screw assemblies 12 and seated within the saddles 34, the set screws 38 may be inserted through the collars 46 and tabs 40 to secure the spine rod 16 in place. Once the set screws 38 are installed, the collars 46 may be individually removed upwardly from the pedicle screw assemblies 12 and the tabs 40 broken along the frangible joints 42 as shown in FIG. 4B and removed from the surgical site.

As a result, a more minimally invasive spinal fixation construct installation procedure is provided by the pedicle screw assemblies, collars and associated devices of this invention without the need for extended incision and associated difficulties. Moreover, increased visualization and minimally invasive disruption are realized with this invention.

From the above disclosure of the general principles of this invention and the preceding detailed description of at least one embodiment, those skilled in the art will readily comprehend the various modifications to which this invention is susceptible. Therefore, we desire to be limited only by the scope of the following claims and equivalents thereof.

We claim:
1. A pedicle screw assembly comprising:
a screw having a threaded shaft and a head;
a body coupled to the screw head and having a channel adapted to receive a spine rod therein;
at least one tab projecting upwardly from the body;
a frangible joint joining the at least one tab to the body such that the tab is adapted to be separated from the body at the frangible joint; and
a collar adapted to be disposed over and releasably mate with the at least one tab extending from the body, the collar including a proximal flange and a sidewall depending from the flange and adapted to telescopically slide over the at least one tab, the sidewall having a first slot extending along an entire length of the sidewall and adapted to provide access to the body of the screw assembly, and a second slot extending along a distal portion of the sidewall opposite the first slot.

2. The pedicle screw assembly of claim 1 further comprising:
a pair of the tabs;
a pair of the frangible joints; and
a pair of spaced arms extending upwardly from the body, the channel being defined between the spaced arms and each of the tabs being coupled to one of the arms along one of the frangible joints.

3. The pedicle screw assembly of claim 2 wherein the pair of tabs are spaced from one another and form a pair of slots there between, each of the slots being in communication with the channel.

4. The pedicle screw assembly of claim 1 wherein the body is a polyaxial body adapted to be positioned in a plurality of orientations relative to a longitudinal axis of the screw shaft.

5. The pedicle screw assembly of claim 1 further comprising:
a set screw adapted to threadably engage the body and capture a rod in the channel.

6. The pedicle screw assembly of claim 1 wherein the at least one tab is elongate and adapted to extend percutaneously from a patient when the screw assembly is inserted into the patient's vertebrae.

7. The pedicle screw assembly of claim 1 further comprising:
a cannula in the screw.

8. The pedicle screw assembly of claim 1 further comprising:
a clocking feature to inhibit relative rotation between the collar and the tab, the clocking feature including two pair of ribs on an exterior surface of the tabs and first and second ribs on an inner surface of the collar, wherein the ribs are positioned such that when the collar is advanced onto the tabs, the first and second ribs on the collar fit between corresponding pairs of ribs on the tabs.

9. The pedicle screw assembly of claim 1 wherein the flange extends transversely from a proximal end of the collar and is configured to be juxtaposed on top of a patient's skin thereby providing a platform for additional devices.

10. The pedicle screw assembly of claim 1 wherein the sidewall has a distal portion and a proximal portion and a midpoint therebetween, wherein the second slot extends only in the distal portion of the sidewall.

11. A pedicle screw assembly comprising:
a screw having a threaded shaft and a head;
a polyaxial body coupled to the screw head being adapted to be positioned in a plurality of orientations relative to a longitudinal axis of the screw shaft;
a pair of spaced arms extending upwardly from the body, a channel being defined between the spaced arms and adapted to receive a spine rod therein;
a pair of elongate tabs each projecting upwardly from an arm and adapted to extend percutaneously from a patient when the screw assembly is inserted into the patient's vertebrae;

a pair of slots formed between the pair of tabs, each of the slots being in communication with the channel;

a pair of the frangible joints each joining one of tabs to an arm such that the tab is adapted to be separated from the arm at the frangible joint;

a collar adapted to be releasably disposed over and mate with the pair of tabs, the collar including a proximal flange and a sidewall depending from the flange and adapted to telescopically slide over the pair of tabs, the sidewall having a distal portion and a proximal portion, the sidewall having a first slot extending along an entire length of the sidewall and adapted to be aligned with one of the slots between the tabs to provide access to the body of the screw assembly, and a second slot extending along the distal portion of the sidewall opposite the first slot and adapted to be aligned with the other one of the slots between the tabs; and a set screw adapted to threadably engage the body and capture the rod in the channel.

12. The pedicle screw assembly of claim 11 further comprising:

a clocking feature to inhibit relative rotation between the collar and the tabs, the clocking feature including at least a first pair of spaced-apart ribs formed on an exterior surface of at least one tab, and at least one corresponding rib formed on an interior surface of the collar, wherein when the collar is disposed over the tabs, the rib on the collar slides between the pair of ribs on the tab.

13. A method of installing a spinal fixation construct onto a patient's spine, the method comprising the steps of:

making a first incision in the patient's skin proximate selected vertebrae of the patient;

inserting first and second screw assemblies into first and second vertebra, respectively, each screw assembly having a tab extending percutaneously from the patient when the screw assembly is inserted into the associated vertebra to retract patient tissue proximate the first incision, the tab having a pair of ribs formed on an exterior surface thereof;

coupling a collar to selected screw assemblies such that a portion of each collar is positioned percutaneously, the collar including a flange extending transversely from a sidewall and a rib formed on an interior surface of the sidewall, wherein coupling the collar to selected screw assemblies includes inserting the collar into the incision and over the screw assemblies with the rib on the collar sliding between the ribs on the tab, until the flange is adjacent the patient's skin;

aligning at least one slot in the sidewall of the collar with at least one slot on the associated screw assembly to thereby provide access for the rod to pass through the respective slots;

inserting a rod through the first incision proximate the tab of at least one of the screw assemblies;

inserting the rod through the slots in the collar and screw assembly;

seating the rod in a channel in each of the screw assemblies;

securing the rod in the channel of each of the screw assemblies; and removing the collar and each of the tabs from the associated screw assembly.

14. The method of claim 13 further comprising:

making a second incision spaced from the first incision;

wherein the first and second screw assemblies are inserted through the first and second incisions, respectively.

15. The method of claim 13 further comprising:

prior to the seating and the securing steps, forming the rod into a desired configuration based on the relative positions of the tabs extending percutaneously from the first and second screw assemblies.

16. The method of claim 13 further comprising:

making a second incision spaced from the first incision and extending proximate a second and a third vertebra;

wherein the first and second screw assemblies are inserted through the first and second incisions, respectively, into the associated vertebrae;

inserting a third screw assembly through the second incision; and inserting the third screw assembly into the third vertebra.

* * * * *